(12) United States Patent
Mohammed et al.

(10) Patent No.: US 11,919,043 B1
(45) Date of Patent: Mar. 5, 2024

(54) INTELLIGENT SORTING FOR DATE PALM FRUIT

(71) Applicant: KING FAISAL UNIVERSITY, Al-Ahsa (SA)

(72) Inventors: Maged Elsayed Ahmed Mohammed, Al-Ahsa (SA); Nashi Khalid Alqahtani, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/226,446

(22) Filed: Jul. 26, 2023

(51) Int. Cl.
*B07C 5/08* (2006.01)
*B07C 5/36* (2006.01)
*G01N 33/02* (2006.01)

(52) U.S. Cl.
CPC ............... *B07C 5/08* (2013.01); *B07C 5/368* (2013.01); *G01N 33/025* (2013.01); *B07C 2501/009* (2013.01)

(58) Field of Classification Search
CPC ..... B07C 5/08; B07C 5/368; B07C 2501/009; B07C 5/363; B07C 5/367; G01N 33/025
See application file for complete search history.

(56) References Cited

U.S. PATENT DOCUMENTS

| | | | | |
|---|---|---|---|---|
| 3,773,172 A | * | 11/1973 | McClure | G01N 33/02 209/912 |
| 3,930,994 A | * | 1/1976 | Conway | B07C 5/3416 209/579 |
| 5,311,998 A | * | 5/1994 | Lerner | B07C 5/36 209/552 |
| 6,998,559 B2 | | 2/2006 | De Baerdemaeker et al. | |
| 10,099,259 B2 | * | 10/2018 | Anup | B07C 5/366 |
| 10,549,317 B2 | * | 2/2020 | Benedetti | B07C 5/342 |
| 11,267,020 B2 | * | 3/2022 | Benedetti | B07C 5/342 |
| 2022/0080465 A1 | | 3/2022 | Giudiceandrea et al. | |
| 2022/0266307 A1 | * | 8/2022 | Benedetti | B07C 5/342 |

FOREIGN PATENT DOCUMENTS

| | | |
|---|---|---|
| CN | 211217573 U | 8/2020 |
| CN | 112775022 A | 5/2021 |
| CN | 213409451 U | 6/2021 |
| CN | 115005400 A | 9/2022 |
| JP | H09037675 A | 2/1997 |
| WO | 2021161341 A1 | 8/2021 |
| WO | 2022182226 A1 | 9/2022 |

OTHER PUBLICATIONS

Wang, Dayuan, et al. "Advanced detection techniques using artificial intelligence in processing of berries." Food Engineering Reviews (2022): 1-24.

* cited by examiner

*Primary Examiner* — Patrick H Mackey
(74) *Attorney, Agent, or Firm* — Nath, Goldberg & Meyer; Richard C. Litman

(57) ABSTRACT

Sorting of produce, such as date palm fruit is achieve by receiving the unsorted fruit, using a plurality of sensors capable of sensing data for determining characteristics of the produce according to criteria comprising size, moisture or moisture content, and color. A control and evaluation unit, responsive to the sensed data, determines the characteristics of the produce and identifies each item of produce according to the characteristics as one of the predetermined categories. An air jet sorter is used to selectively divert the produce to the different ones of the output bins or ports according to the identified category for that produce.

13 Claims, 7 Drawing Sheets

US 11,919,043 B1

INTELLIGENT SORTING FOR DATE PALM FRUIT

BACKGROUND

Technical Field

The present disclosure relates to automatic sorting of fruit and other agricultural products, using machine learning techniques. The techniques are particularly well-suited for automated sorting of date palm fruit, such as Mejhoul, Sukary, Khalas, and Ajwa dates.

Background Art

While there are approximately 400 date palm fruit varieties, as with many fruits, culinary dates received by a given processor will be of a single variety, the most common being the Mejhoul date (*Phoenix dactylifera*).

As with many fruits and produce, dates are classified according to their quality. In the case of dates or date palm fruit, they can be classified into three groups: ripe (Tamr), which is typically amber to dark brown with the moisture content of <25%, unripe (Besr), and Low Quality. Dates that are rejected for use as whole fruit (Low Quality) may be perfectly suitable for further processing for culinary use, for example for use as a date spread. In many cases, though, Low Quality fruit may not be suitable for culinary use. The date classification is based on color, size, and moisture content, but requires the observation of an experienced sorter. While manual classification has traditionally been used, it would be advantageous to accomplish such classification in an automated process.

The nature of dates is such that common automated sorting techniques are often not effective. Traditionally, such sorting is accomplished manually by skilled sorters who are able to quickly distinguish between qualities of the fruit related to ripeness, size, general quality, and the like. Translating this process to machinery is difficult because it becomes difficult to calibrate sorters for some of the desired qualities of dates. Additionally, while dates are frequently batch harvested, the individual fruit does not necessarily ripen simultaneously, resulting in a mixture of ripeness and fruit maturation within a particular batch.

SUMMARY

Produce is automatically sorted by receiving the produce in a receiving bin or port for transfer to an intake conveyer and passing the produce through a plurality of sensors capable of sensing data. The sensing data is used for determining characteristics of the produce, comprising predetermined categories according to criteria including size, moisture or moisture content, and color. A control and evaluation unit, responsive to the sensed data, is used to determine the characteristics of the produce and identify each item of produce according to the characteristics as one of the predetermined categories. The control and evaluation unit controls an air jet sorter so as to cause the air jet sorter to selectively divert the produce to the different ones of output bins or ports according to the identified category for that produce.

In a non-limiting example, the produce to be sorted comprises date palm fruit.

In a further configuration, the sorting is performed by sequentially sorting the produce, thereby eliminating sorting criteria in subsequent sorting operations, providing more accuracy in earlier sorting operations by applying criteria for that sorting operation independent of further sorting operations, and providing more accuracy in later sorting operations by eliminating produce in the earlier categories from the later sorting operations.

BRIEF DESCRIPTION OF THE DRAWINGS

FIG. 1 is a side view of the date fruit sorting machine. FIG. 2 is a plan view.

DETAILED DESCRIPTION

Figure 1:
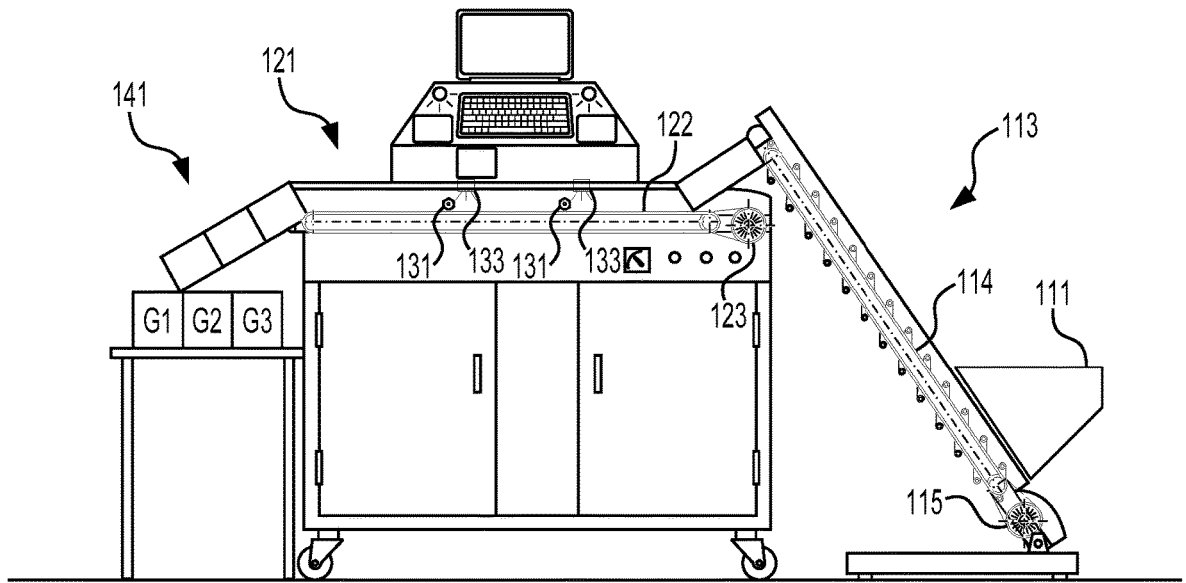
FIGS. 1 and 2 are schematic diagrams of the Intelligent Sorting Machine for Date Palm Fruit (ISMD).

In general, the present disclosure is directed to an apparatus for sorting produce. The apparatus includes a receiving bin or port, an intake conveyer, a plurality of sensors capable of sensing data for determining characteristics of the produce with the characteristics including predetermined categories according to criteria comprising size and at least one additional characteristic, a plurality of output bins or ports, at least one air jet sorter capable of selectively diverting the produce to different ones of the output bins or ports, and a control and evaluation unit, responsive to the sensed data to determine the characteristics of the produce and identify each item of produce according to the characteristics as one of the predetermined categories, and control the air jet sorter so as to cause the air jet sorter to selectively divert the produce to the different ones of the output bins or ports according to the identified category for that produce.

The control and evaluation unit determines the characteristics of the produce and identify each item of produce according to the characteristics as one of the predetermined categories, and controls the air jet sorter to selectively divert the produce to the different ones of the output bins or ports by: determining whether the produce has reached a deflection area, and if the produce has reached the deflection area, activates deflection solenoid valves after a predetermined delay consistent with a transit time of the produce from the deflection area; determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and controlling the air jet sorter to sort the produce according to the predetermined categories.

It is also contemplated that the control and evaluation unit performs the sorting by sequentially sorting the produce, thereby eliminating sorting criteria in subsequent sorting operations, providing more accuracy in earlier sorting operations by applying criteria for that sorting operation independent of further sorting operations, and providing more accuracy in later sorting operations by eliminating produce in the earlier categories from the later sorting operations.

The control and evaluation unit further: determines the characteristics of the produce and identifies each item of produce according to the characteristics as one of the predetermined categories, and controls the air jet sorter to selectively divert the produce to the different ones of the output bins or ports by: determining whether the fruit has reached a deflection area, and if the fruit has reached the deflection area, activates deflection solenoid valves after a predetermined delay consistent with a transit time of the fruit from the deflection area; determining if the fruit has reached a sensor area, and in the case of the fruit not having reached the sensor area after a predetermined delay, deactivating a feed conveyer and providing an error indication, and in the case of the fruit having reached the sensor area, taking measurements to determine color, moisture content, and size, and identifying the fruit according to predetermined categories; and controlling the air jet sorter to sort the fruit according to the predetermined categories.

The control and evaluation unit performs a sorting step to sense Besr category fruit, in which the fruit meets a predetermined early level of ripeness, and after performing the sorting step to sense Besr category fruit, the control and evaluation unit performs a sorting step to sense Tamr category fruit, in which the fruit has reached a further level of ripeness beyond the Besr category fruit, or has a predetermined lower moisture content. The control and evaluation unit assigns fruit not sensed as Besr category fruit and not sensed as Tamr category fruit to a Low Quality classification.

The present disclosure is also directed to a method for sorting produce. The sorting method includes: receiving produce at bin or port and directing the produce into an intake conveyer; sensing data for determining characteristics of the produce, the characteristics comprising predetermined categories according to criteria comprising size and at least one additional characteristic; selectively diverting the produce to different ones of the output bins or ports by use of an air jet sorter; determining the characteristics of the produce and identifying each item of produce according to the characteristics as one of the predetermined categories responsive to the sensed data; and controlling an air jet sorter so as to selectively divert the produce to the different ones of the output bins or ports according to the identified category for that produce.

The present disclosure is further directed to a computer program product for sorting produce. The computer program product has a non-transitory computer-readable medium. The non-transitory computer-readable medium includes: a first instruction for determining characteristics of the produce, the characteristics comprising predetermined categories according to criteria comprising size and at least one additional characteristic; a second instruction for determining the characteristics of the produce and identifying each item of produce according to the characteristics as one of the predetermined categories responsive to the sensed data; and a third instruction for controlling an air jet sorter so as to selectively divert the produce to the different ones of the output bins or ports according to the identified category for that produce.

Also included are instructions determining the characteristics of the produce and identifying each item of produce according to the characteristics as one of the predetermined categories, and controlling the air jet sorter to selectively divert the produce to the different ones of the output bins or ports by: determining whether the produce has reached an deflection area, and if the produce has reached the deflection area, activates the air jet sorter after a predetermined delay consistent with a transit time of the produce from the deflection area; determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and controlling the air jet sorter to sort the produce according to the predetermined categories.

In a particular aspect of the present disclosure, the disclosed technology relates to an intelligent sorting machine involving hardware and software components that work together to automate a complex task for accurately evaluating and sorting fruit such as dates. As used herein, "dates," "date fruit," and "date palm fruit" are used interchangeably. More specifically, the disclosed technology includes an intelligent sorting machine that separates dates according to their quality into three groups: ripe (Tamr, G1), unripe (Besr, G2), and Low Quality (G3). The dates are sorted for color, size, and moisture content. The sorting employs programmable controllers by using combined sensors. The classification is achieved by use of a machine that includes various components for sensing, processing, and sorting the dates such as a computer, microcontroller, multi-sensors, and air pressure-based distribution units (air jet sorters) used as sorting mechanisms for moving the dates to different bins based on their quality.

The machine is programmed with artificial neural networks (ANN) based software systems to process data from the sensors and make decisions about the quality of each date fruit. The software also controls the solenoid air valves of the sorting mechanisms to move the dates from a conveyor to appropriate bins. The machine also includes a user interface to allow operators to interact with it and monitor its performance. Statistics may be displayed showing information, including without limitation the number of dates sorted, the percentage of high-quality dates, and alerts for errors or malfunctions.

The feeding unit, conveyor belt, and frame structure may be made of any suitable material for food handling, such as stainless steel. Stainless steel has the advantage of being easy to clean and sanitize, and allows easy removal of sugar and fruit residue.

The machine may include a feedback mechanism to improve its performance over time. If the machine misclassifies date fruit, it could be programmed to learn from the mistake and adjust its artificial neural network algorithms accordingly. By accurately and efficiently sorting dates, the machine can improve productivity and profitability of date fruit sorting operations and ensure only highest quality date fruit makes it to market.

While the present description is directed to sorting of dates, the disclosed techniques are not limited to only date and can be useful for a variety of fruits and produce for which automated sorting is desired.

Figure 2:
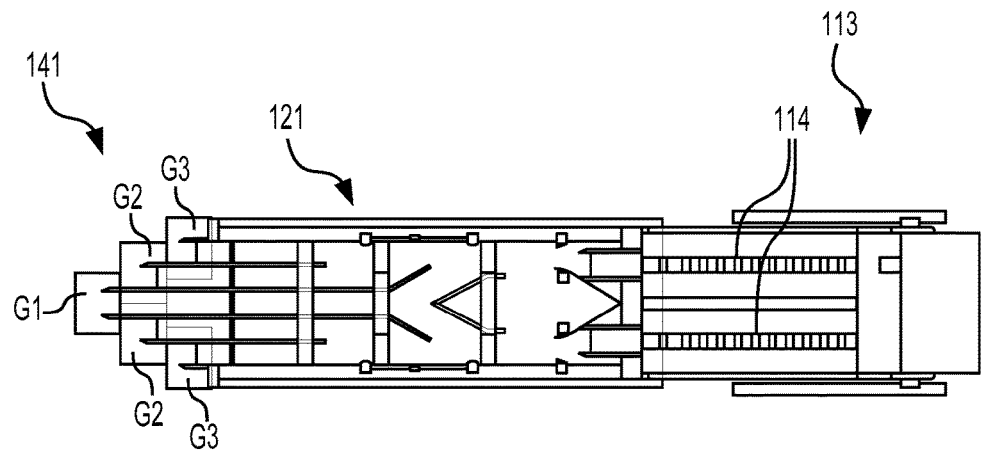

A prototype of the Intelligent Sorting Machine for Date Palm Fruit (ISMD) according to a non-limiting embodiment of the present disclosure was designed, constructed, and evaluated in a workshop at the Date Palm Research Center of Excellence, King Faisal University, Al-Ahsa, Saudi Arabia. FIGS. 1 and 2 are schematic diagrams of the Intelligent Sorting Machine for Date Palm Fruit (ISMD). FIG. 1 is a side view of the date fruit sorting machine. FIG. 2 is a plan view.

The ISMD includes at least three main units; a feeding unit, an intelligent sorting unit, and an air pumping unit. The following description and dimensions are of a demonstration unit and is intended to describe the basic operation of the ISMD. It is anticipated that full scale operation includes suitable modifications for expediting large scale sorting and operation.

Mechanically, the feeding unit comprises a conveyor belt and a hopper. The conveyor belt is a rubber strip with 0.03 cm thickness and 250 cm length linked with one drive pulley and another driven pulley. Each pulley is installed to the feeding system frame by two ball bearings. The external diameter of each ball bearing is 58 mm, and the internal diameter is 20 mm. The rubber qualities are 60±5 hardness (share), 30 M Pa/2Ply tensile strength, and 300% elongation. The power transmission system for operating the conveyor belt includes two pulleys; the first set is installed on the motor shaft (drive pulley), and the second is installed on the front roller (driven pulley), and motion transmits by the drive belt. The motor speed reduction is conducted mechanically using small and large pulley wheels to reduce the motor speed to the required speed for the conveyor belt.

The final design of the ISMD is constructed after conducting several preliminary experiments to reach the optimal feeding speed at which different sections are to be operated, the durability of the materials for withstanding the speed, fixing of the color, size, and moisture content sensors and illumination chamber to produce diffused light, actuators for sorting the fruit to multiples groups, such as, by way of non-limiting example, three groups. This final design can be used to test the robustness of the system. Pieces of rubber with a diameter of 2 cm and width of 5 cm were installed on the conveyor belt at 10 cm (two lines) to convey the fruit from the hopper to the sorting unit with the optimum angle of 55°. The mechanical system of the feeding unit is designed for a throughput of 1 to 5 fruit per second for each line. The efficiency of the ISMD was tested at speeds of 1, 2, 3, 4, 5, and 6 fruit/sec. The electrical motor of 0.5 HP, a motorized geared unit with 1440 rpm output, was selected to operate the main conveyor assembly of the feeding unit. The motor speeds were changed using a variable speed driver with a Volte/frequency control transducer (model XSY-AT2, 2.2 kw, China) to adjust the fruit feeding rate at the target feeding rate. The feeding hopper is made of stainless-steel sheets with a thickness of 0.1 cm and external dimensions of 40×40×35 cm (at a maximum height). The bottom surface is tilted at an angle of 42 degrees to ensure that all fruit is transferred from the hopper to the sorting unit. It is noted that all of the dimensions described herein are given by way of non-limiting example, as the specific configuration is a matter of design choice. Additionally, the example is that of a demonstrator model and does not take into consideration the requirements for large scale commercial operation inherent in commercial agriculture processing. As such, equipment of other dimensions can be used to accomplish the tasks described herein.

Depicted in FIGS. 1 and 2 are feeding hopper 111, feeding unit 113, conveyer belt 114 for feeding unit 113 and conveyer belt motor 115. Also shown is sorting unit 121, conveyer belt 122 for sorting unit 121 and conveyer belt motor 123. Within feeding unit 113 are sensors 131 and cover 133 to control light intensity. Output section 141 has gates identified as G1 for Tamr (ripe), G2 for Besr (unripe), and G3 for Low Quality.

The intelligent sorting unit includes the frame and transmission, lighting chamber, deflection and distribution system, and sensor and control system. The frame of the sorting unit is constructed from equal-sided angle stainless steel 4 cm side-length and 2 cm thickness and square shape (4×4 cm) with 0.2 cm thickness welded together to connect all sorting components. The frame dimensions for this demonstration model are 120×55×155 cm in length, width, and height, respectively. The frame is covered with stainless steel sheets, making it a box to protect the conveyor belt and the electronic components. The frame cover is constructed from a stainless steel sheet with 0.1 cm thickness. The dimensions of this box are 55×90×150 cm. Free four wheels are fixed in the bottom of square shape stainless steel (4×4 cm) with 0.2 cm thickness and 55 cm length at each corner. The bars are welded at the bottom of the main frame. The conveyor belt is made of rubber strips with a 0.3 cm thickness and 250 cm length and attached with two rollers. Each roller is connected to the sorting unit frame by ball bearings. The external diameter of each ball bearing is 5.5 cm, and the internal diameter is 2 cm. The rubber qualities are 60±5 hardness (share), 30 M Pa/2Ply tensile strength, and 300% elongation. The speed reduction unit (power transmission system) is used to reduce the motor speed to the required speed for the conveyor belt. In addition, the motor speeds were changed using a variable speed driver with a voltage/frequency control transducer (Banggood Model XSY-AT2 2.2KW Single Phase 220V Input and Single-Phase Out Frequency Converter, China) to properly adjust the belt speed to the target feeding rate. The most appropriate speed for this conveyor was selected to be at least 20% higher than the speed of the feeding conveyor to ensure that the fruit is not overcrowded and that the fruit is separated if more than one fruit is loaded in one holder using the air jet sorters for fruit deflection.

In order to evaluate fruit color, uniform illumination is used. Lighting is a significant component in the sorting unit, and light source selection is an important factor in lighting system design. Illumination uniformity over the field of view and spectral composition of the light are primary considerations for measuring fruit color. In the demonstration unit, a white LED light source is used due to its spectral advantage. For fixing the light in the sensing area, a lighting chamber is made of a stainless steel sheet with a thickness of 0.1 cm with lower base dimensions of 48×75 cm, upper surface dimensions of 48×48, and a height of 30 cm. Two white LED strips with a length of 40 cm and a power of 20 watts (for each one) were installed on the upper surface of the lighting chamber in addition to the lighting that is installed in the sensor units. It is recognized that lighting units having different spectral characteristics may be selected in order to provide advantages in sorting capabilities.

Figure 3:
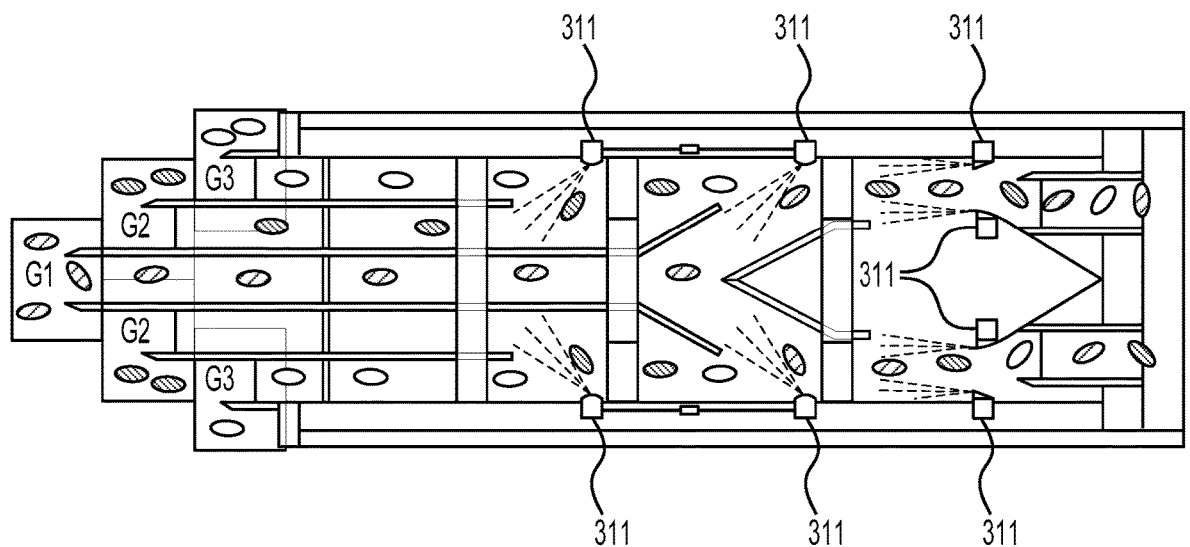
FIG. 3 is a schematic diagram of a deflection and distribution system, showing sorting date palm fruit.

FIG. 3 is a schematic diagram of a deflection and distribution system, showing sorting date palm fruit. The deflection and distribution system includes four pneumatic solenoid valves, such that, when 12v DC current is applied, the valve opens to allow air through. The system used a frame of five gates made of stainless steel with a thickness of 1 mm, and four air jet sorters for fruit deflection before entering the sensing area.

Depicted are gates G1 for Tamr (ripe), G2 for Besr (unripe), and G3 for Low Quality. Air jet sorters 311 deflect the fruit according to category.

For air jet sorters 311, the adjusted compressed air is discharged through the converging nozzle from the compressor tank with the tested air pressure levels of 100, 150, and 200 kPa to select the optimum pressure. The results indicated that the pressure of 150 kPa was optimal, so it was applied to sort the dates at the inlet area of each nozzle was 78.5 mm², and the exit area was 5 mm². The flow rate, air consumption, and force on the nozzle outlet were calculated using the following equations, assuming isentropic flow in the nozzle and the air to behave as a perfect gas with a constant ratio of specific heats (γ) of 1.4. The experiments were conducted at a controlled air temperature of 23° C. The air temperature in the compressor tank ranged from 23 to 25° C.

Mass air flow for moving the detected fruit to the target position was calculated using the following equation:

$$\dot{m} = \rho_e A_e V_e$$

$$= \left(\frac{\delta_p P_A}{R \times \Theta_t \times T_A}\right) A_e \left(M_e \sqrt{\gamma R \Theta_t T_A}\right)$$

where $\dot{m}$ is the mass flow rate of the air through a nozzle (kg s⁻¹), $\rho_e$ is air density at the exit area of the nozzle (kg m⁻³), $A_e$ is exit area of the nozzle (m²), $V_e$ is the velocity of mass flow through the nozzle exit area (m s⁻¹), $\delta_p$ is the critical-pressure ratio ($\delta_p$=0.5283), $P_A$ is the applied air pressure (kPa), R is the gas constant of air (R=0.287 kPa m³ kg⁻¹ K⁻¹), $\Theta_t$ is the temperature ratio ($\Theta_t$=0.833), $T_A$ is the applied air temperature (K), $M_e$ is the Mach number at the exit area of the nozzle, γ is the ratio of specific heats of the air (γ=1.4).

The required aerodynamic force for moving the detected fruit to the target position was calculated using the following equations:

$$F = F_d - F_{fric}$$

$$F_d = \frac{1}{2}\rho_a A_p v^2 C_d$$

$$C_d = \frac{F_{fric}}{v_c^2 A_p \rho_a}$$

$$F_{fric} = m_f g \mu_f$$

where F is the required aerodynamic force (N), $F_d$ is the aerodynamic drag force (N), $F_{fric}$ is the frictional force (N), $\rho_a$ is the air density ($\rho_a$=1.176 kg m⁻³ at a temperature of 25° C.), $A_p$ is projected area in a longitudinal direction of the fruit (m²), v is air velocity in the target position (m s⁻¹), $C_d$ is the dimensionless drag coefficient, $v_c$ is the critical velocity (air velocity (m s⁻¹) that was reached when the frictional force and air resistance were equalized on the tested fruit), $m_f$ is the mass of the tested fruit (kg), g is the acceleration due to gravity (g=9.81 m s⁻¹), $\mu_f$ is a dimensionless coefficient of static friction.

Figure 4:
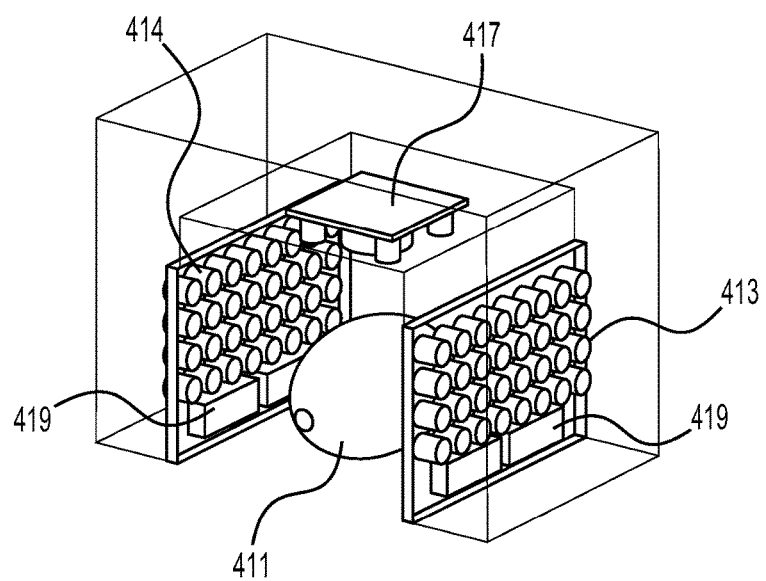
FIG. 4 is a schematic diagram of the sensors unit of the ISMD.

FIG. 4 is a schematic diagram of sensors unit of the ISMD. The figure shows the sensors unit of the ISMD that contain the size, moisture content, and color sensors. Depicted are target date fruit 411, infrared transmitters 413, infrared receivers 414 and color sensors 417.

The date palm fruit size sensor is a non-contact sensor that uses infrared technology to measure the projected area of a date palm fruit as a function of the fruit size. This sensor consists of 32 IR transmitters 413 and 32 IR receivers 414 that are arranged in a four-by-eight grid. Transmitters 413 send infrared rays, and receivers 414 receive them on the other side. When a date palm fruit is present, the infrared rays are blocked according to the size and shape of the fruit. Receivers 414 measure the blocked rays, and this information is used to calculate the projected area of the fruit. The projected area of the fruit is used to determine its size. The larger the projected area, the larger the fruit size. The sensor data is used to measure the fruit's size in real time and as input to an artificial neural network (ANN) model. The sensor is very accurate and could measure the size of date palm fruit with high precision at 5 fruit/sec. for the demonstrator unit.

The induction-based sensor is used to determine the moisture levels of the fruit accurately. The emitter of the sensor emits an electromagnetic field penetrating the fruit and interacting with its structure. As the moisture content of the fruit increases or decreases, the electrical properties of the fruit change, resulting in changes in the electromagnetic field. The sensor receiver then measures these changes and calculates the fruit's moisture content. The sensor data is used to measure the fruit's size in real time and as input to the ANN model.

The color sensor for date palm fruit is a non-contact sensor that uses an RGB (red, green, and blue) photoelectric sensor (TCS3200 Color Sensor, from Texas Advanced Optoelectronic Solutions Inc., of Plano, Texas), which emits light from a transmitter and then detects the light reflected from the detected date palm fruit with a receiver. The color sensor for date palm fruit works by measuring the light reflected off the fruit's surface. The sensor has three light sensors, one for each primary color (RGB). The sensor measures the light reflected off the fruit's surface for the three primary colors. The sensor then uses these measurements to calculate the color of the fruit. The color sensor detected the received light intensity for RGB, respectively, making it possible to determine the color of the target fruit. The sensor is used to measure the color of date palm fruit in real time as input to the ANN model. The color sensor is very accurate and could measure the color of date palm fruit with a high degree of precision. The sensors are provided with filters to reject unwanted IR light.

Figure 5:
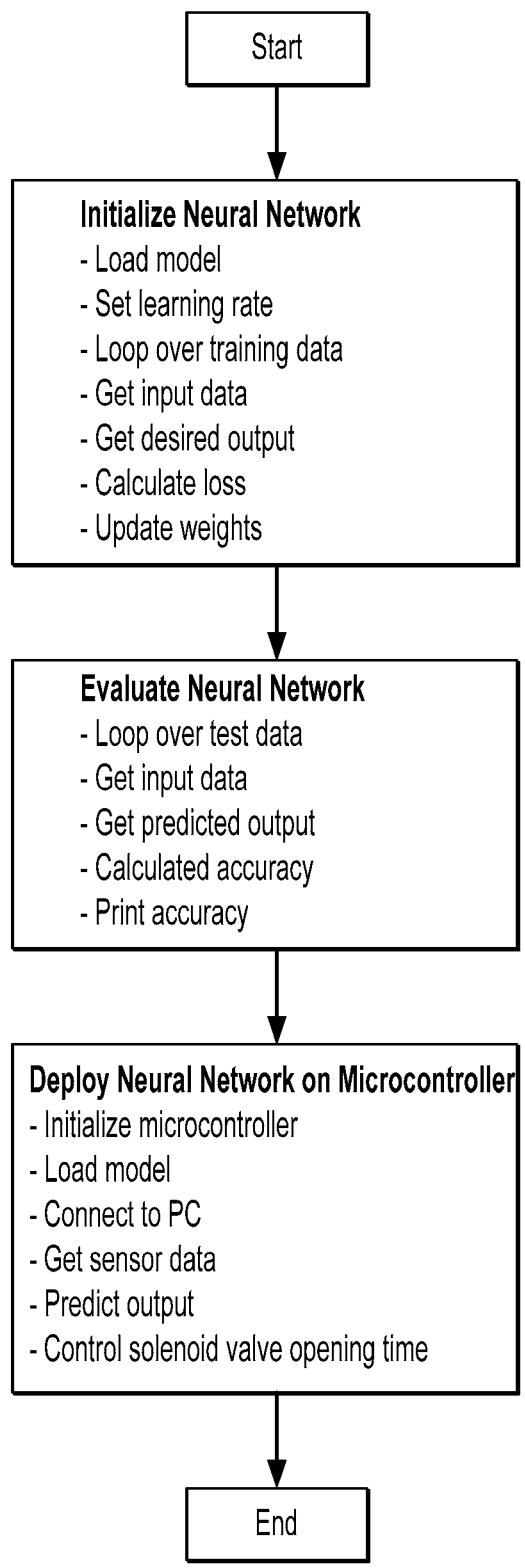
FIG. 5 is a flow diagram outlining the major steps of the code for sorting one category of date fruit.

FIG. 5 is a flow diagram outlining the major steps of the code for sorting one category of date fruit. An ATmega2560 microcontroller (Microchip Technology Inc., Chandler, Arizona, USA) was used for each sensor unit to control one air solenoid valve as a versatile and powerful microcontroller, which provides microprocessor functions, which in turn functions as a control and evaluation unit. This microcontroller allows for simultaneous access to program memory and data memory. Therefore, four ATmega2560 microcontrollers have been used for fruit sorting (G1 and G2). The ATmega2560 has many built-in peripherals, including timers, watchdog timers, an 8-channel 10-bit ADC, and a USART for serial communication. The flow diagram of FIG. 5 outlines the major steps of code to implement the functions of the ATmega2560 microcontroller.

The ISMD supplied the required compressed air using an air pump unit. The air pump unit uses a compressor (model N100/E2.8/2, Saudi Arabia) equipped with a 1.5 kw/220 V electric motor and two positive displacement piston-cylinder. The reservoir capacity of the air compressor was 0.1 m³ with air pressure up to 600 kPa. The compressor tank was large enough to produce no changes in the tank temperature and pressure when the air was exhausted through the four jet sorters. An air pressure regulator was used to provide a constant pressure outlet at 200 kPa, separately from the air pressure in the compressor tank, to minimize pressure variation, reduce the air pressure to the required level, protect the equipment, and stabilize the force applied to pneumatic solenoid valves (model JVL, China) of the distribution and deflection system.

The artificial intelligence and the use of a neural network to sort the fruit in accordance with machine learning is accomplished by the use of various samples. The samples include fruit that was pre-sorted in order to identify the different grades or qualities to be sorted in order to classify the fruit. In that way, the human selection of the samples can be "learned" by pre-identifying the fruit and allowing the sensors to scan the fruit of the known grades or qualities to classify the fruit. The criteria used by the sorter need not be pre-identified, but rather based on the classification provided to the ISMD. The machine learning is achieved by tie ISMD scanning fruit of different classifications.

It is anticipated that, after the machine learning, the classification by the ISMD may in fact vary from the results of hand classification. If that variation is acceptable, review of the sorting in order to update the model can take into consideration whether the classification by the ISMD is acceptable, or even possibly superior to hand classification.

As a sample collection, a mixture of the tested ripe (Tamr), unripe (Besr), and Low Quality date palm fruit was randomly hand-harvested in the season of 2021 from an orchard located at the Training and Research Station, Date Palm Research Center of Excellence, King Faisal University, KSA (fruit harvested from, Latitude 25.268196° N, Longitude 49.708468° E, and Altitude 155 m). The harvested fruit was a mixture of three groups, i.e., Tamr, Besr, and Low Quality. Tamr fruit is fully ripe date palm fruits with brown to dark brown color. Besr fruit is unripe date palm fruit with yellow to yellowish-brown that can be artificially ripened. The Low Quality fruit such as unripe fruit that cannot become ripe artificially or are strange or non-conforming fruit such as unpollinated dates. Low Quality fruit is characterized by immature characteristics such as light color or greenish-yellow, lightweight, absence of pits, rubbery texture, and thin flesh. The mixture date fruit was immediately cleaned after harvesting with compressed air at 100 kPa and stored in the cold storage room at 18° C. for initial physical analyses. Then the experiments were conducted at a temperature of 25° C.

Figure 6A:
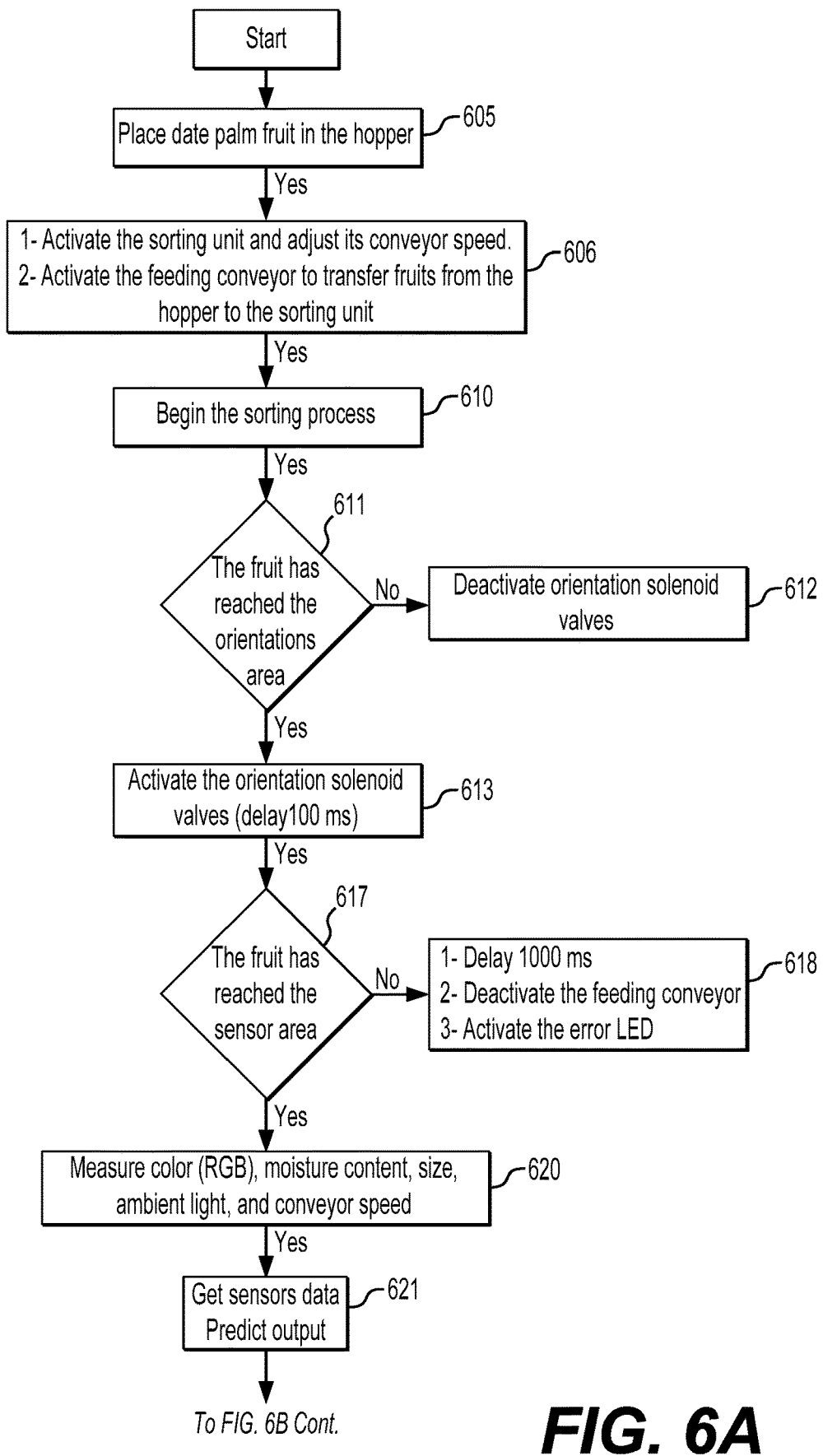
FIGS. 6A and 6B are a flow diagram showing a process of the one line of the ISMD system
Figure 6B:
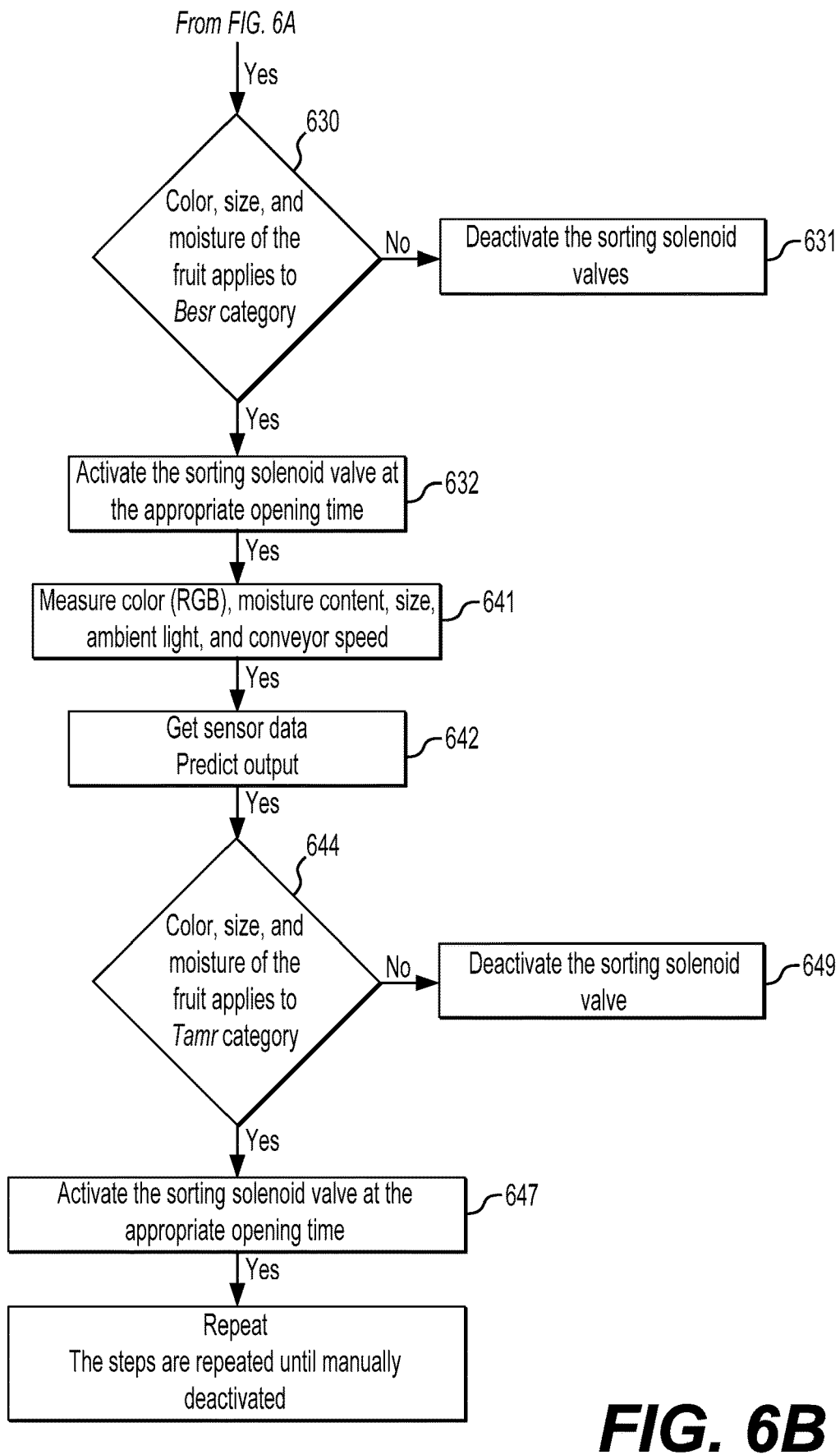

FIGS. 6A and 6B are a flow diagram showing a process of the one line of the ISMD system, showing the steps used in the overall process of the ISMD system. After START, the fruit is placed in the hopper (step 605). the sorting unit is activated and its conveyer speed is adjusted as required. The feed conveyer is activated to transfer the fruit from the hopper to the sorting unit (step 606).

The sorting process is then begun (step 610). A determination is made (step 611) of whether the fruit has reached the deflection area. If not, the deflection solenoid valves are deactivated (step 612). If the fruit has reached the deflection area, the deflection solenoid valves are activated (step 613) after a predetermined delay (in the example 100 ms) consistent with the transit time of the fruit from the deflection area.

A determination (step 617) is made if the fruit has reached the sensor area. If the fruit has not reached the sensor area after a predetermined delay (1000 ms in the example), after which the feed conveyer is deactivated and an error indication is provided (step 618). If the fruit has reached the sensor area measurements are taken to determine color, moisture content, and size, taking into account ambient light and conveyer speed (step 620) and the sensor data is used to predict the output (step 621).

With the sensor data obtained and the output predicted (steps 620 and 621), sorting is performed based on the fruit being identified as Besr category and Tamr category. To sense Besr category fruit, color, size, and moisture of the fruit obtained from the sensor data is applied to the criteria for Besr category fruit. For fruit which is not categorized as Besr, the sorting solenoid valve is deactivated (step 631) which allows the fruit to continue to the next sorting step. For fruit which is categorized as Besr, the solenoid valve is activated (step 632), sorting the fruit as Besr.

To sense Tamr category fruit, color, size and moisture of the fruit obtained from the sensor data is applied to the criteria for Tamr category fruit. For fruit which is not categorized as Besr, the sorting solenoid valve is deactivated (step 634) which allows the fruit to continue to the next sorting step. For fruit which is categorized as Tamr, the solenoid valve is activated (step 635), sorting the fruit as Tamr. The remaining fruit is not classified, and therefore continues to the Low Quality classification.

While the steps for Besr and Tamr are described as sequential operations, these steps can be combined, thereby causing the fruit to be sorted in a single operation. Likewise, the activation or deactivation according to Besr and Tamr, or activation according to Low Quality can be applied differently to sort the fruit, as the physical sorting function does not depend on the specific category.

The use of sequential sorting has the advantage of eliminating sorting criteria in subsequent sorting steps, thereby providing more accuracy in earlier sorting steps by applying criteria for that sorting step independent of further sorting steps, and providing more accuracy in later sorting steps by eliminating fruit in the earlier categories from the later sorting steps.

The steps described in the flow diagram of FIGS. 6A and 6B start with a model of the categories as detected by the sensors. The model can be established in any convenient manner, such making adjustments to the responses to the sensed data. Alternatively, manually sorted fruit can be separately provided to the ISMD sorter for each category, and the respective categories and identified to the ISMD. Since the manually sorted fruit is of a single category, the ISMD need only identify that category for at least a majority of the fruit, on the assumption that the machine shorting should closely reflect manual sorting. This would enable the ISMD itself to identify the criteria for identifying each category as a machine learning process. In practice, however, once this identification of categories is performed, this creates a model, so that future batches of fruit in multiple categories can be sorted. Once the model is established, the model can be used as a starting model for additional machines of the same configuration and with similar sensors. The model can also be used when increasing the sorting speed, by using the model as a starting point when calibrating the ISMD for the increased speed.

As noted, the air valves open after a time delay in the process. The distribution system consists of air solenoid valves and a jet sorter with a specific direction to push the sorted fruit to the correct gate. The air valve opening time is based on the fruit size and the sorting belt speed. Therefore, the air valves are opened for a more extended period for larger fruit and a shorter period for smaller fruit.

Figure 7:
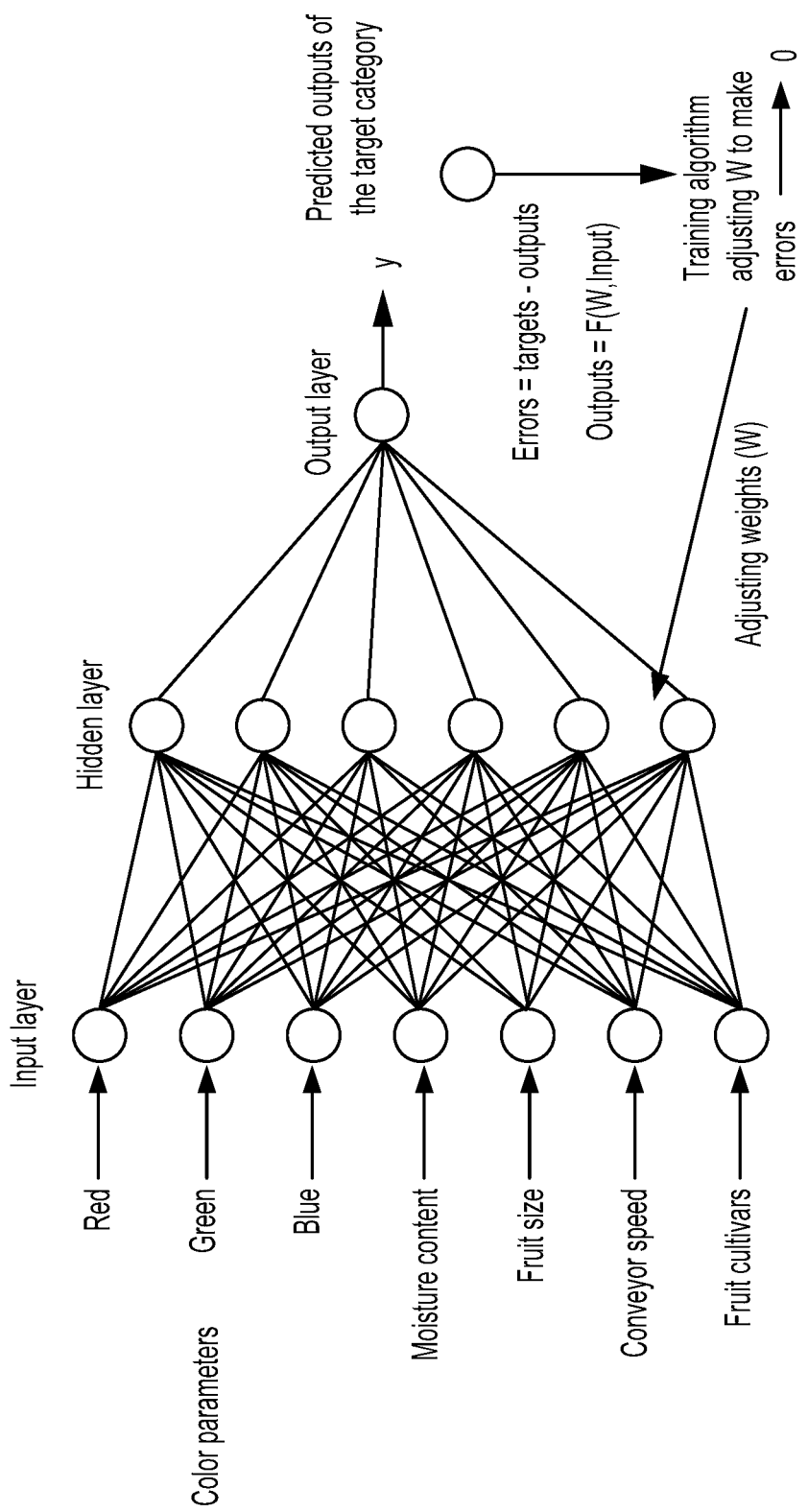
FIG. 7 is a schematic diagram of an algorithm/artificial neural network (ANN) architecture using an ANN-based intelligent system.

FIG. 7 is a schematic diagram of an algorithm/artificial neural network (ANN) architecture using an ANN-based intelligent system. In order to improve efficiency of the sorting operation, an ANN can be used. The ANN can be used in the implementation of steps described in connection with the flow diagram o FIGS. 6A and B, and the ANN facilitates improving the process over time.

In the main architecture of the ANN model, the input is provided for the date palm fruit according to the palm fruit variety as a model for that palm fruit variety. The appropriate value is entered according to the date palm fruit variety before operating the machine), sorting speed data, ambient light intensity data, color sensor data (RGB), moisture content sensor data, and size sensor data. The output is the air valve opening time of the suitable air jet sorter air valve for fruit classification into the target category.

The flow diagram shows the major steps involved in improving an ANN model over time, including data selection, storage, anomaly detection, classification, training, and prediction. The process begins with data acquisition and storage, followed by identifying anomalies in the stored data. The system then classifies the data based on the normal size, moisture, and color ranges, and trains the ANN model to optimize its predictions. The trained model is then used to predict the fruit category based on input sensor data, and the air solenoid valve opening time is adjusted accordingly. This process is iteratively repeated as new data becomes available, allowing the ANN model to improve over time and provide more accurate predictions continually. The process involves the following processes:

1—The date palm fruit is fed into the system constantly based on fruit cultivars.
2—The air directs the fruit toward the sensors to ensure that the date fruit is evenly spaced and all in the same orientation.
3—The fruit is then passed through the three sensors that measure their moisture content, color, and size.
4—The data from the moisture content, color, size, ambient light intensity, feeder speed, and sorting belt speed sensors are then fed into an ANN to recognize the fruit class.
5—The ANN then classifies the fruit into the target group of Tamr or Besr, and Low-Quality no action needed.
6—The fruit is directed to the appropriate gate based on date palm fruit classification.

Figure 8:
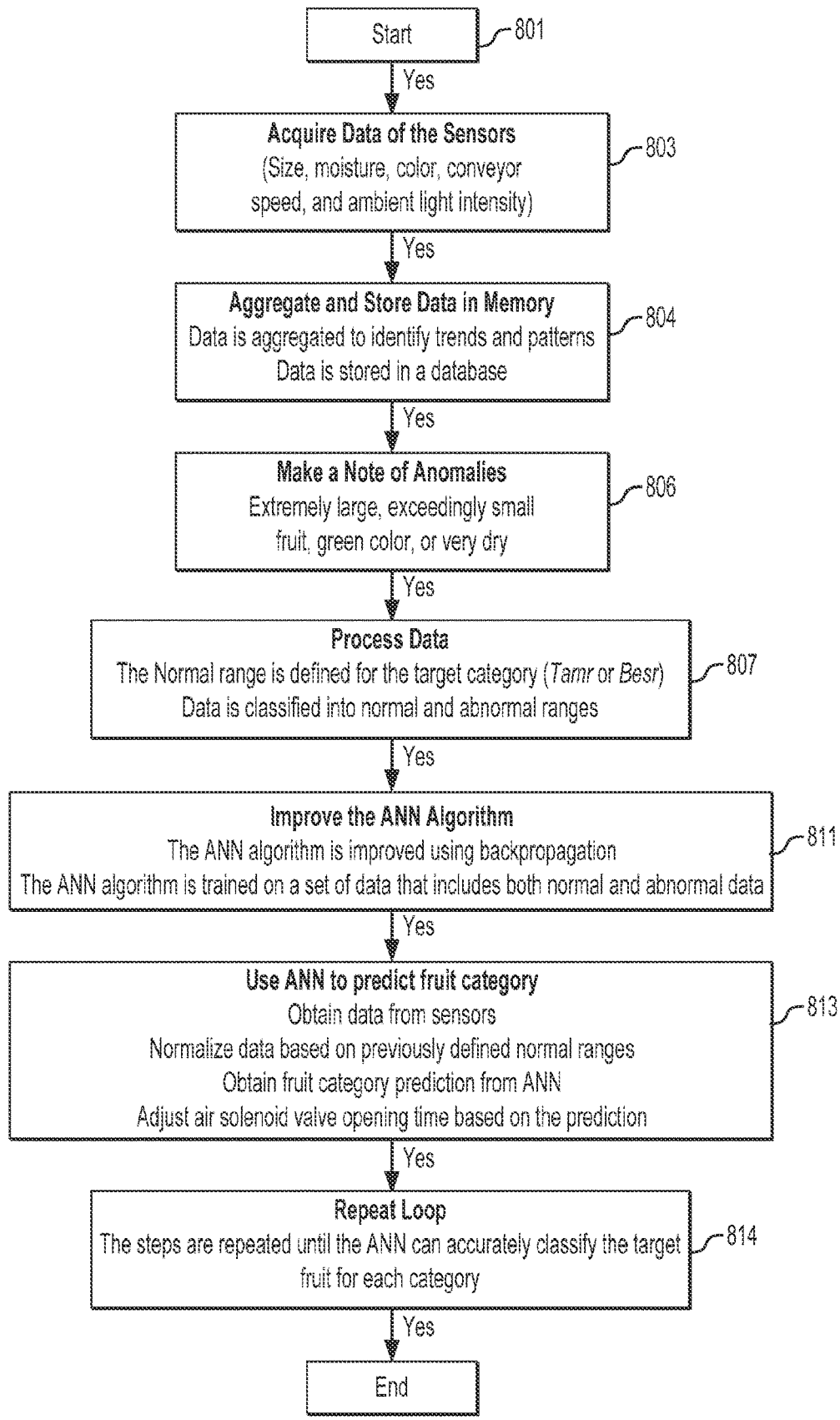
FIG. 8 is a flow diagram showing specific steps taken by the algorithm and the artificial neural network to improve over time.

FIG. 8 is a flow diagram showing specific steps taken by the algorithm and the artificial neural network to improve over time. After START (step 801), data from the sensors is acquired (step 803) related to size, moisture and color, taking into account conveyor speed and ambient light intensity. The data is aggregated and stored in memory (step 804). Anomalies are identified (step 806). Non-limiting examples of anomalies are excessively large, excessively small fruit, color anomalies including green fruit (Khalal) and excessively dry fruit. These are determined to be Low-Quality, or are otherwise diverted for special purposes.

The data is then processed (step 807) to determine the category of the fruit. The ANN algorithm is improved based on back-propagation of data (step 811). The ANN is used to predict (step 813) based on data obtained from the sensor, and normalized based on previously defined ranges. The loop is repeated on an ongoing basis (step 814).

Closing Statement

The disclosed examples directed to sorting of date fruit are given as non-limiting examples. It is possible to implement the disclosed techniques for other fruit and other produce, in particular where a determination of quality and classification involves multiple factors. Examples include other tree fruit, such as olives, and fruit which are harvested in various states of ripeness.

In the case of date fruit, while classifications of Besr and Tamr have been described, the disclosed techniques can be used for other classifications, including, by way of non-limiting examples, unripe categories of Hababawk, Kimri, Khalal, and to separately categorize Besr into Besr and ripe, but not dried varieties of Rutab (typically light brown with 30-45% moisture content).

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. Apparatus for sorting produce, comprising:
a receiving bin or port;
an intake conveyer;
a plurality of sensors capable of sensing data for determining characteristics of the produce, the characteristics comprising predetermined categories according to criteria comprising size and at least one additional characteristic;
a plurality of output bins or ports;
at least one air jet sorter capable of selectively diverting the produce to different ones of the output bins or ports;
a control and evaluation unit, responsive to the sensed data to determine the characteristics of the produce and identify each item of produce according to the characteristics as one of the predetermined categories, and control the air jet sorter so as to cause the air jet sorter to selectively divert the produce to the different ones of the output bins or ports according to the identified category for that produce; and
a plurality of said air jet sorters sequentially arranged so as to perform separate sorting operations for sequential characteristics of the produce,
wherein the control and evaluation unit determines the characteristics of the produce and identify each item of produce according to the characteristics as one of the predetermined categories, and controls the air jet sorter to selectively divert the produce to the different ones of the output bins or ports by:
determining whether the produce has reached a deflection area, and if the produce has reached the deflection area, activates deflection solenoid valves after a predetermined delay consistent with a transit time of the produce from the deflection area;
determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and
controlling the air jet sorter to sort the produce according to the predetermined categories.

2. The apparatus of claim 1, wherein the control and evaluation unit performs the sorting by sequentially sorting the produce, thereby eliminating sorting criteria in subsequent sorting operations, providing more accuracy in earlier sorting operations by applying criteria for that sorting operation independent of further sorting operations, and providing more accuracy in later sorting operations by eliminating produce in the earlier categories from the later sorting operations.

3. The apparatus of claim 1, wherein the sorting produce comprises sorting date palm fruit.

4. The apparatus of claim 3, wherein the control and evaluation unit:
  determines the characteristics of the produce and identifies each item of produce according to the characteristics as one of the predetermined categories, and controls the air jet sorter to selectively divert the produce to the different ones of the output bins or ports by:
  determines whether the fruit has reached a deflection area, and if the fruit has reached the deflection area, activates deflection solenoid valves after a predetermined delay consistent with a transit time of the fruit from the deflection area;
  determines if the fruit has reached a sensor area, and in the case of the fruit not having reached the sensor area after a predetermined delay, deactivating a feed conveyer and providing an error indication, and in the case of the fruit having reached the sensor area, taking measurements to determine color, moisture content, and size, and identifying the fruit according to predetermined categories; and
  controls the air jet sorter to sort the fruit according to the predetermined categories.

5. The apparatus of claim 4, wherein control and evaluation unit performs the sorting by sequentially sorting the fruit, thereby eliminating sorting criteria in subsequent sorting steps, providing more accuracy in earlier sorting steps by applying criteria for that sorting step independent of further sorting steps, and providing more accuracy in later sorting steps by eliminating fruit in the earlier categories from the later sorting steps.

6. The apparatus of claim 5, wherein the control and evaluation unit performs a sorting step to sense Besr category fruit, in which the fruit meets a predetermined early level of ripeness, and after performing the sorting step to sense Besr category fruit, the control and evaluation unit performs a sorting step to sense Tamr category fruit, in which the fruit has reached a further level of ripeness beyond the Besr category fruit, or has a predetermined lower moisture content,
  and wherein the control and evaluation unit performs assigns fruit not sensed as Besr category fruit and not sensed as Tamr category fruit to a Low-Quality classification.

7. A method for sorting produce, comprising:
  receiving produce at bin or port and directing the produce into an intake conveyer;
  sensing data for determining characteristics of the produce, the characteristics comprising predetermined categories according to criteria comprising size and at least one additional characteristic;
  selectively diverting the produce to different ones of the output bins or ports by use of an air jet sorter;
  determining the characteristics of the produce and identifying each item of produce according to the characteristics as one of the predetermined categories responsive to the sensed data;
  controlling an air jet sorter so as to selectively divert the produce to the different ones of the output bins or ports according to the identified category for that produce;
  arranging a plurality of said air jet sorters sequentially so as to perform separate sorting operations for sequential characteristics of the produce; and
  determining the characteristics of the produce and identifying each item of produce according to the characteristics as one of the predetermined categories, and controlling the air jet sorter to selectively divert the produce to the different ones of the output bins or ports by:
  determining whether the produce has reached an deflection area, and if the produce has reached the deflection area, activates the air jet sorter after a predetermined delay consistent with a transit time of the produce from the deflection area;
  determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and
  controlling the air jet sorter to sort the produce according to the predetermined categories.

8. The method according to claim 7, further comprising sequentially sorting the produce, thereby eliminating sorting criteria in subsequent sorting operations, providing more accuracy in earlier sorting operations by applying criteria for that sorting operation independent of further sorting operations, and providing more accuracy in later sorting operations by eliminating produce in the earlier categories from the later sorting operations.

9. The method according to claim 7, wherein the sorting produce comprises sorting date palm fruit.

10. The method according to claim 9, further comprising determining the characteristics of the produce and identifying each item of produce according to the characteristics as one of the predetermined categories, and controlling the air jet sorter to selectively divert the produce to the different ones of the output bins or ports by:
  determining whether the produce has reached an deflection area, and if the produce has reached the deflection area, activates the air jet sorter after a predetermined delay consistent with a transit time of the produce from the deflection area;
  determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and
  controlling the air jet sorter to sort the produce according to the predetermined categories.

11. The method according to claim 10, further comprising sequentially sorting the fruit, thereby eliminating sorting criteria in subsequent sorting steps, providing more accuracy in earlier sorting steps by applying criteria for that sorting step independent of further sorting steps, and providing more accuracy in later sorting steps by eliminating fruit in the earlier categories from the later sorting steps.

12. The method according to claim 11, comprising a sorting step to sense Besr category fruit, in which the fruit meets a predetermined early level of ripeness, and after performing the sorting step to sense Besr category fruit, the control and evaluation unit performs a sorting step to sense Tamr category fruit, in which the fruit has reached a further level of ripeness beyond the Besr category fruit, or has a predetermined lower moisture content, and wherein the control and evaluation unit performs assigns fruit not sensed as Besr category fruit and not sensed as Tamr category fruit to a Low-Quality classification.

13. A computer program product for sorting produce, the program comprising:
   a non-transitory computer-readable medium comprising:
   a first instruction for determining characteristics of the produce, the characteristics comprising predetermined categories according to criteria comprising size and at least one additional characteristic;
   a second instruction for determining the characteristics of the produce and identifying each item of produce according to the characteristics as one of the predetermined categories responsive to the sensed data;
   a third instruction for controlling an air jet sorter so as to selectively divert the produce to the different ones of the output bins or ports according to the identified category for that produce; and
   a fourth instruction for determining the characteristics of the produce and identifying each item of produce according to the characteristics as one of the predetermined categories, and controlling the air jet sorter to selectively divert the produce to the different ones of the output bins or ports by:
   determining whether the produce has reached an deflection area, and if the produce has reached the deflection area, activates the air jet sorter after a predetermined delay consistent with a transit time of the produce from the deflection area;
   determining if the produce has reached a sensor area, and in the case of the produce not having reached the sensor area after a predetermined delay, deactivating a feed conveyer and providing an error indication, and in the case of the produce having reached the sensor area, taking measurements to determine color, moisture content, and size, and identifying the produce according to predetermined categories; and
   controlling the air jet sorter to sort the produce according to the predetermined categories.

* * * * *